US005931868A

United States Patent [19]
Gross

[11] Patent Number: 5,931,868
[45] Date of Patent: Aug. 3, 1999

[54] METHOD OF FIXING A PHYSIOLOGIC MITRAL VALVE BIOPROSTHESIS

[75] Inventor: Jeffrey M. Gross, Mission Viejo, Calif.

[73] Assignee: Medtronic, Inc., Minneapolis, Minn.

[21] Appl. No.: 08/969,035

[22] Filed: Nov. 12, 1997

Related U.S. Application Data

[62] Division of application No. 08/629,179, Apr. 8, 1996, abandoned.

[51] Int. Cl.$^6$ ........................................ A61F 2/24
[52] U.S. Cl. ................................................ 623/2
[58] Field of Search .............................. 623/2, 900, 901, 623/66

[56] References Cited

U.S. PATENT DOCUMENTS

| | | | |
|---|---|---|---|
| 4,261,342 | 4/1981 | Duo ........................................ | 128/1 R |
| 4,350,492 | 9/1982 | Wright et al. ........................... | 8/94.11 |
| 4,443,895 | 4/1984 | Lane ....................................... | 3/1.5 |
| 4,960,424 | 10/1990 | Grooters ................................. | 623/2 |
| 5,080,670 | 1/1992 | Imamura et al. ....................... | 623/2 |
| 5,554,184 | 9/1996 | Machiraju .............................. | 623/2 |

FOREIGN PATENT DOCUMENTS

| | | | |
|---|---|---|---|
| 42 34 127 A1 | 5/1994 | Germany .......................... | A61F 2/24 |
| WO 92/03990 | 3/1992 | WIPO ............................... | A61F 2/24 |
| 9220303 | 11/1992 | WIPO ............................... | A61F 2/24 |

OTHER PUBLICATIONS

C. Acar, M.D., et al., "Technique of Homograft Replacement of the Mitral Valve", *Journal Heart Valve Disease*, vol. 4, No. 1, Jan. 1995, pp. 31–34.

J. Bernal, M.D., et al., "Letters to the Editor titled 'Mitral Valve Homografts'", *Journal Heart Valve Disease*, vol. 4, No. 1, Jan. 1995, pp. 47–48.

D. Cosgrove, M.D., "Editorial: Mitral Homograft for Tricuspid Valve Replacement", *Journal Heart Valve Disease*, 2(2):124, Mar. 1993.

G. DeLaria, M.D., et al., "Hemodynamic Evaluation of a Bioprosthetic Venous Prosthesis", *Journal of Vascular Surgery*, 18(4):577–86, Oct. 1993.

Carlos M.G. Duran, M.D., "Editorial: Mitral Valve Allografts. An Opportunity", *The Journal of Heart Valve Disease*, 1995;4:29–30.

T. Fischlein, et al., "Integrity and Viability of Homograft Valves", *European Journal of Cardiothoracic Surgery* (1994) 8:425–430.

A. Kumar, et al., "Homograft Mitral Valve Replacement—A Case Report", *The Journal of Heart Valve Disease*, 1994;3: 473–475.

L. Mickleborough, M.D., et al., "A Simplified Concept for a Bileaflet Atrioventricular Valve that Maintains Annular–Papillary Muscle Continuity" *JCS*, 4:58–68, Mar. 1989.

Donald N. Ross, "Evolution of the Homograft Valve—Special Presentation", *Annals of Thoracic Surgery*, 59:565–7, (1995).

M. Morea, et al., "Mitral Valve Replacement with the Bicor Stentless Mitral Valve: Early Results", *The Journal of Heart Valve Disease*, 1994;3:476–482.

(List continued on next page.)

*Primary Examiner*—Michael J. Milano
*Attorney, Agent, or Firm*—Harold R. Patton; Peter Forrest

[57] ABSTRACT

A whole heart is collected shortly after the death of the animal. The left ventricle and left atrium of the animal heart is sectioned and exposed thereby exposing the mitral valve, the chordae tendineae and the papillary heads. The mitral valve is fixed in situ by fixing portions of the left ventricle and left atrium containing the mitral valve. The mitral valve is excised from the animal heart remnant to include a portion of the endocardium containing the papillary heads and the annulus. In the preferred embodiment of the invention, the excised mitral valve is further fixed to complete fixation of the papillary heads. Then, the excess myocardial tissue is trimmed away and the mitral valve is stored in fixing solution to await further processing.

19 Claims, 5 Drawing Sheets

OTHER PUBLICATIONS

Y. Okita, M.D., et al., "Analysis of Left Ventricular Motion After Mitral Valve Replacement with a Technique of Preservation of all Chordae Tendineae", *J Thorac Cardiovasc Surg*, 1992;104:786–95.

Y. Okita, M.D., et al., "Comparative Evaluation of Left Ventricular Performance After Mitral Valve Repair of Valve Replacement With or Without Chordal Preservation", *J Heart Valve Dis*, 2 (2):159–166. Mar. 1993.

H. Oku, M.D. et al., "Semilunar Valve Replacement with a Cylindrical Valve", *Journal of Cardiac Surgery*, 8(6):666–70. Nov., 1993.

J. Pomar, M.D., PhD, et al., "Tricuspid Valve Replacement Using a Mitral Homograft—Surgical Technique and Initial Results", *The Journal of Heart Valve Disease*, 1993;2:125–128.

D. Salter, M.D., et al., "Papillary–Annular Continuity and Left Ventricular Systolic Function after Mitral Valve Replacement", *Circulation*, vol. 74 (suppl l), Sep. 1986, pp. 121–129.

H. Vetter, M.D., et al. "Mitral Allograft with Chordal Support: Echocardiographic Evaluation in Sheep", *The Journal of Heart Valve Disease*, 1995;4:35–39.

H. Vetter, M.D., et al., "In Vitro and In Vivo Examination of a New Design of a Stentless Chordally Supported Mitral Valve Allograft", *New Horizons and the Future of Heart Valve Bioprostheses*, First Edition, Silent Partners, Inc. Austin ©1994.

M. Vrandecic, et al., "Anatomically Complete Heterograft Mitral Valve Substitute: Surgical Technique and Immediate Results", *The Journal of Heart Valve Disease*, 1992;1:254–259.

M. Vrandecic, M.D., et al., "Heterologous Mitral Valve Transplant: The First 50 Patients Clinical Analysis", *European Journal of Cardio–Thoracic Surgery* (1995) 9:69–74.

Mihailo Vucinic, "Suspension of the Papillary Muscles during Valve Replacement for Mitral Stenosis" *The Journal of Heart Valve Disease*, 2(3):311–313:93 May.

A. Yankah, et al., "Clinical Report on Stentless Mitral Allografts", *The Journal of Heart Valve Disease* 1995; 4:40–44.

Gross, Jeffrey M. "Physiologic Mitral Valve Bioprosthesis" Patent Application filed Dec. 1, 1995, USSN 08/566,229.

METHOD OF FIXING A PHYSIOLOGIC MITRAL VALVE BIOPROSTHESIS

This application is a division of application Ser. No. 08/629,179 filed Apr. 8, 1996 which application is now abandoned.

BACKGROUND OF THE INVENTION

1. Field of the Invention

The invention relates to xenograft heart valves and more particularly relates to a method of fixing a xenograft mitral heart valve for use in humans.

2. Description of Related Art

Heart valves from human cadavers, so called "homograft" valves, have been implanted in living human recipients for at least thirty years. Evolution of the Homograft Valve, Donald N. Ross, Special Presentation, Annals of Thoracic Surgery 59:565–7 (1995). A primary problem with homograft valves is their availability. By contrast, heart valves from animals, so called "xenograft" valves, particularly from pigs, cows and sheep, are abundant. Porcine xenograft heart valves have been collected, treated and implanted in humans to replace damaged or defective human heart valves since at least the early 1970s.

Porcine aortic heart valves have been found to be particularly good replacement heart valves for humans. One reason for this is that the porcine aortic heart valve has many similarities in both size and structure to the aortic valve in human hearts.

With respect to the mitral valve, a porcine mitral valve of a certain annular size generally has chordae tendineae slightly shorter than the chordae tendineae of the human mitral valve it replaces with a similar annular size. This problem has been solved, as disclosed in my co-pending U.S. patent application Ser. No. 08/566,229 titled "Physiologic Mitral Valve Bioprosthesis" filed Dec. 1, 1995, by fashioning a porcine mitral xenograft valve that is suitable for human implant.

Throughout this disclosure, the term "subvalvular" means the part of the heart below the annulus of the mitral valve including the chordae tendineae and papillary heads and the term "annulus" means the part of the heart where the leaflets are inserted into the endocardium or inner wall of the heart.

Many factors can be used to choose the porcine mitral valve to be implanted in the human. Many candidate porcine valves are rejected because their shape, cosmetic appearance, or chordal distribution and geometry are not desirable. If any of these characteristics is altered during the fixation process, the once desirable valve would become unusable. The method of fixing a mitral valve such that its annulus and subvalvular geometric structure is not altered during the fixation process is a problem in need of a solution.

A method for fixing a porcine xenograft mitral valve has been tried by M. P. Vrandecic et. al. Anatomically Complete Heterograft Mitral Valve Substitute: Surgical Technique and Immediate Results, Journal of Heart Valve Disease 1992;1:254–259. Vrandecic's method uses a surgical technique to harvest the mitral valve immediately after slaughter in order to preserve the integrity of the mitral valve. The valve is then fixed using zero pressure fixation. However, in removing the valve from the heart prior to fixation, the valve may suffer geometric distortion because of the lack of the left ventricular tethering function which serves to maintain mitral valve geometry. The result may be a valve that fatigues prematurely due to unnatural stress distributions in the leaflets, annulus or the subvalvular apparatus. Therefore, the problem still exits as to how to fix a xenograft mitral valve in its natural configuration.

SUMMARY OF THE INVENTION

A whole heart is collected shortly after the death of the animal. The left ventricle and left atrium of the animal heart is sectioned and exposed thereby exposing the mitral valve, the chordae tendineae and the papillary heads. The mitral valve is fixed in situ by fixing portions of the left ventricle and left atrium containing the mitral valve. During this initial fixation, the excess myocardium not integral to the mitral valve is used to maintain the unique geometry of the mitral valve while the mitral valve is being fixed.

The mitral valve is excised from the animal heart remnant to include a portion of the endocardium containing the papillary heads and the annulus. In the preferred embodiment of the invention, the excised mitral valve is further fixed to complete fixation of the papillary heads. Then, the excess myocardial tissue is trimmed away and the mitral valve is stored in fixing solution to await further processing. The processing could include adding a cloth covering to the mitral valve's annulus and adding a cloth covering to the mitral valve's papillary heads.

It is a primary object of the invention to provide a method of fixing a xenograft mitral valve.

It is a further object of the invention to provide a method of fixing a xenograft mitral valve that maintains the correct relative orientation and geometry of the various parts of the mitral valve.

It is another object of the invention to provide a method of fixing a xenograft mitral valve that produces a mitral valve that mimics the healthy native human mitral valve.

It is another object of the invention to provide a method of fixing a xenograft mitral valve that is easy to perform.

It is another object of the invention to provide a method of fixing a xenograft mitral valve that produces a mitral valve that is easy to implant.

It is yet another object of the invention to provide a method of fixing a xenograft mitral valve that produces a mitral valve that is strong and durable.

These and other objects of the invention will be clear with reference to the attached drawings and the following detailed description of the invention. Throughout this description, like elements, wherever referred to, are referenced by like reference numbers.

DETAILED DESCRIPTION OF THE INVENTION

Figure 1:
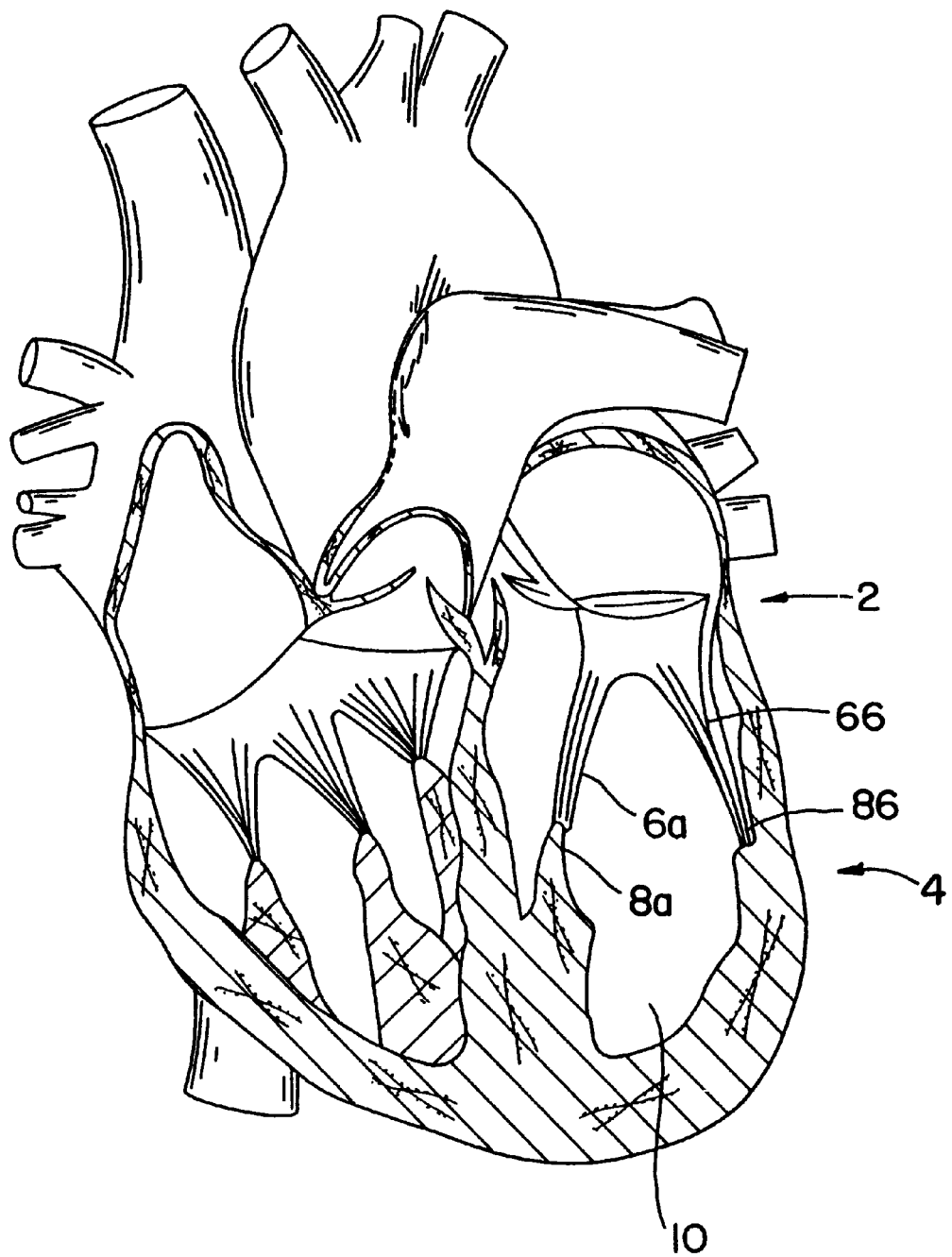
FIG. 1 is a cutaway view of a human mitral valve in position in a human heart.

A healthy human mitral valve is shown in FIG. 1 generally labeled 2 within a human heart 4. Two sets of chordae tendineae 6a, 6b connect mitral valve 2 to corresponding papillary heads 8a, 8b within the left ventricle 10 of heart 4. Occasionally, the mitral valve 2 becomes defective or injured and needs to be replaced. It is often desirable to use a xenograft mitral heart valve as a replacement for the defective human mitral valve. Such a xenograft mitral valve is disclosed in my co-pending U.S. patent application Ser. No. 08/566,229 titled "Physiologic Mitral Valve Bioprosthesis" filed Dec. 1, 1995.

In the following description, a porcine xenograft valve is shown. The porcine xenograft is for illustrative purposes only; the invention includes a method for fixing all xenograft mitral valves including, but not limited, to bovine and ovine mitral valves.

Figure 2:
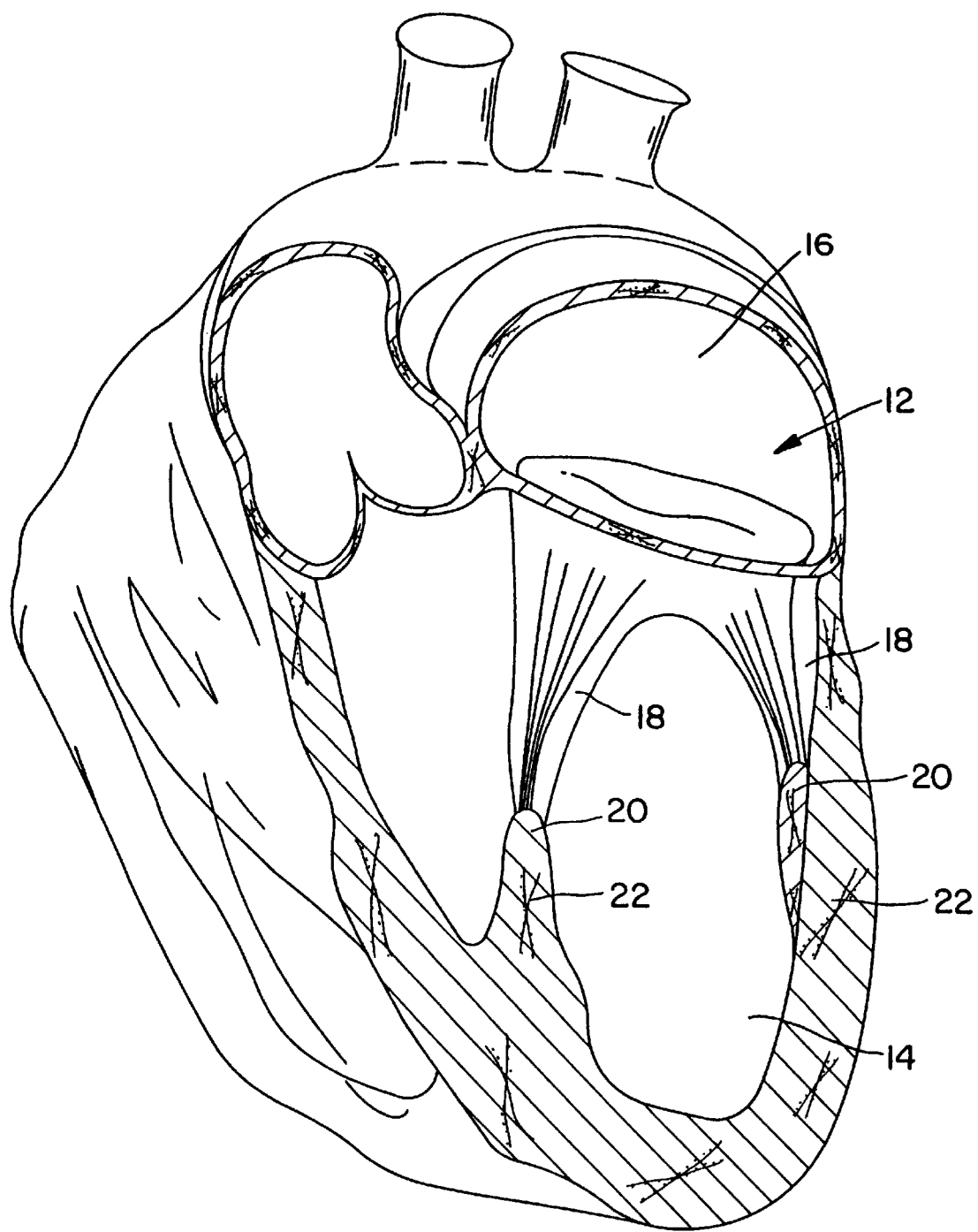
FIG. 2 is a cutaway view of a porcine mitral valve in position in a pig heart.

A porcine mitral valve is shown in position in a pig heart in FIG. 2 generally labeled 12. Valve 12 is fixed in preparation for making a porcine xenograft valve for implant into a human as follows. The whole pig heart is collected shortly after the death of the pig. The left ventricle 14 and left atrium 16 of the pig heart is sectioned and exposed thereby exposing the mitral valve 12, the chordae tendineae 18 and the papillary heads 20. Sectioning means cutting the pig heart in a plane parallel to the mitral valve annulus to open the left atrium and bisect the septum and aortic valve to open the left ventricle without damaging the mitral valve.

The porcine mitral valve 12 is preliminary fixed in situ by fixing portions of the left ventricle 14 and left atrium 16 containing the mitral valve 12 by techniques well known in the art. These techniques include but are not limited to zero pressure, low pressure, and high pressure glutaraldehyde fixation, carbodyamide fixation, epoxide fixation or a combination of these with or without other tissue matrix preserving techniques.

Figure 3:
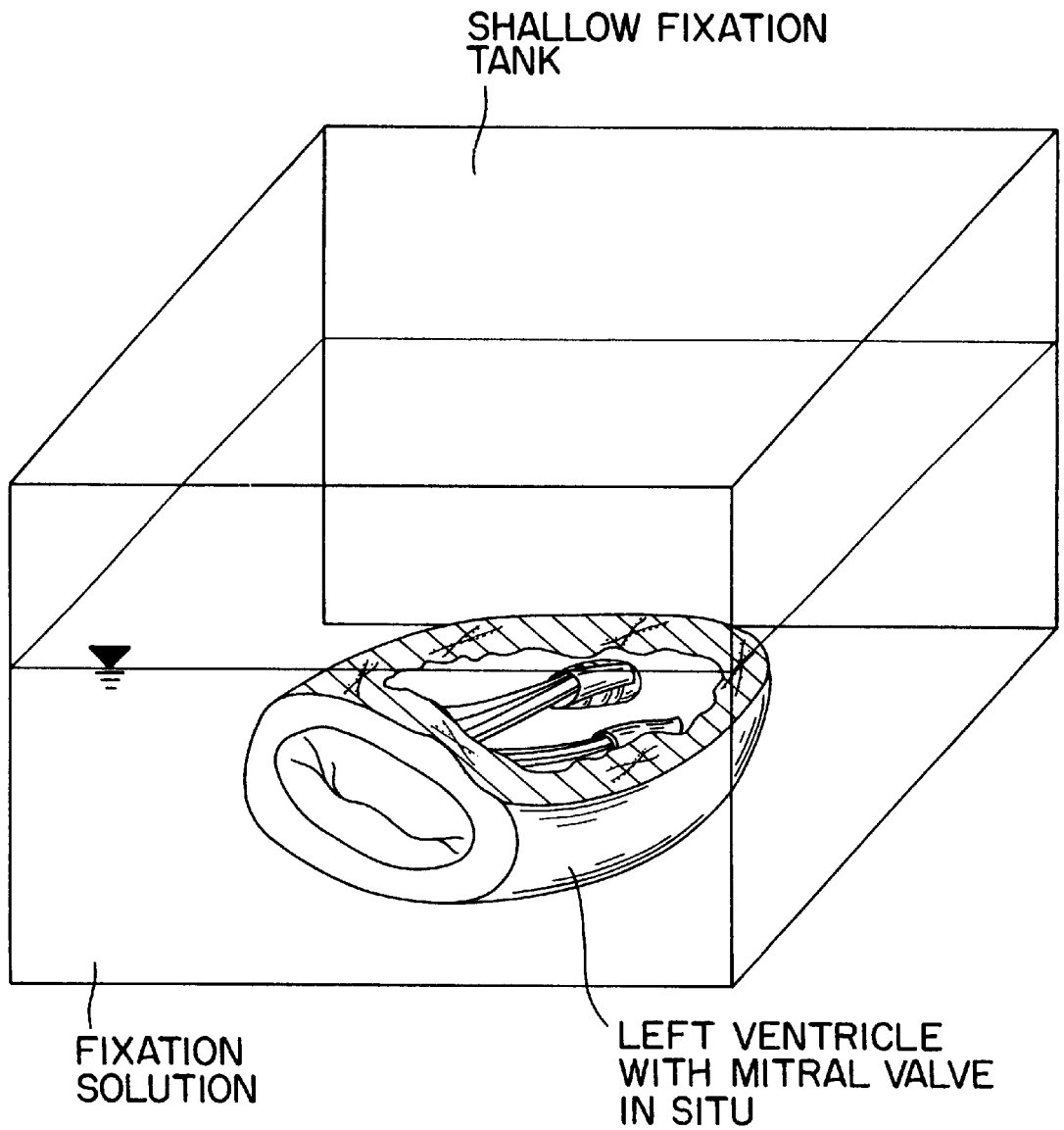
FIG. 3 is a perspective view of a porcine mitral valve in a pig heart placed in a zero pressure fixation chamber.

FIG. 3 shows this in situ fixing procedure being performed with the zero pressure fixation technique. The reason for this preliminary fixation in situ is to preserve the unique geometry of the mitral valve without requiring the entire heart to be fixed under pressure. It is burdensome to fix the entire heart because the mitral valve cannot be inspected prior to fixation if the heart remains intact. As approximately ten hearts are presently required to obtain one good mitral valve, fixing mitral tissue that cannot be used is both cost and time prohibitive. Nevertheless, if desired, the whole heart may be fixed by applying pressure to the entire left heart in the presence of a tissue fixation agent. Regardless of the way achieved, the key is to fix the mitral valve to render it non-immunogenic, biocompatible, and structurally stable.

In the initial fixation, the excess myocardium not integral to the mitral valve 12 is used to maintain the unique geometry of the mitral valve 12 while the mitral valve 12 is being fixed. After the initial fixation, the mitral valve maintains its shape as a result of stiffening due to the fixation agent or agents. Thus, the excess myocardium can be discarded.

Figure 4:
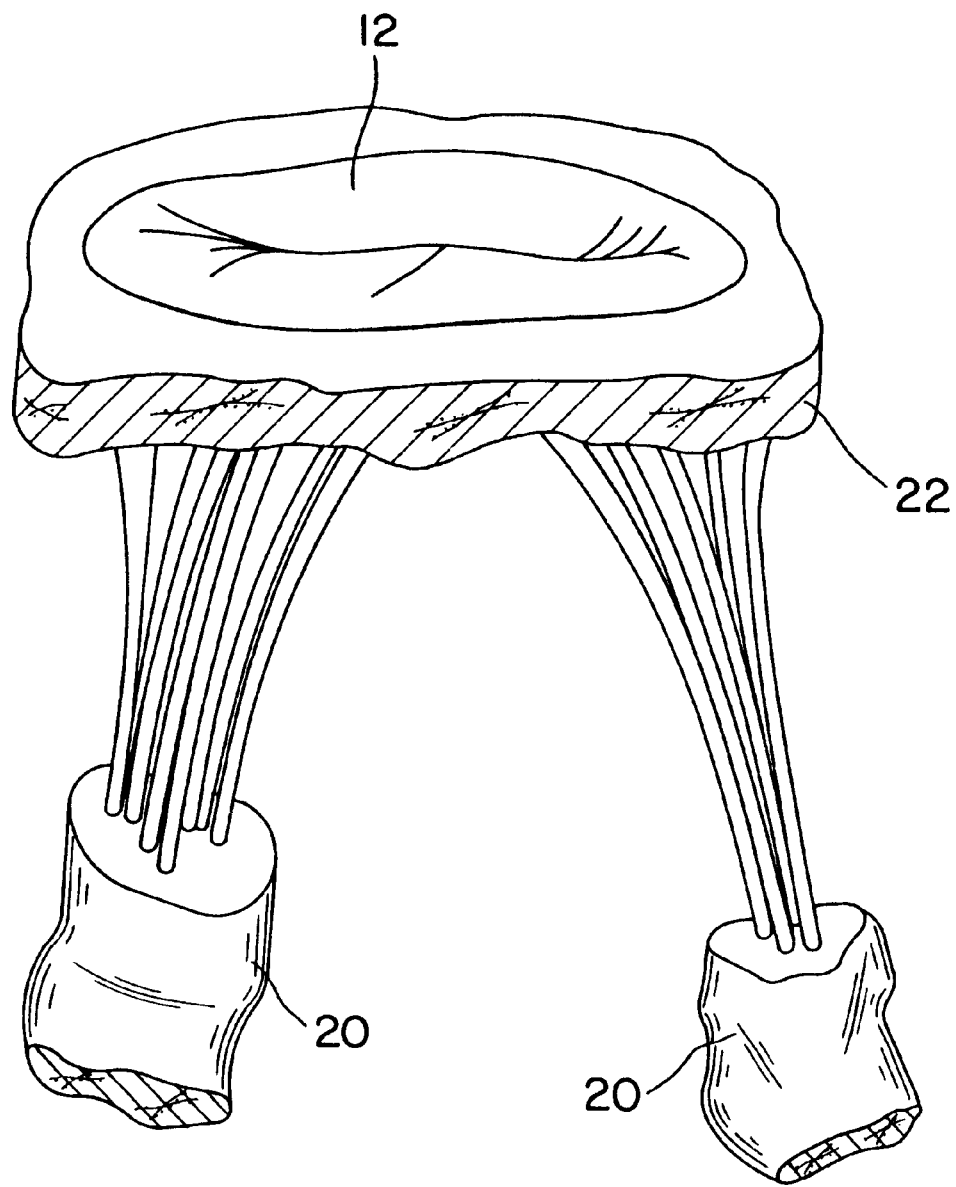
FIG. 4 is a perspective view of a rough dissection of the fixed porcine mitral valve.

The mitral valve 12 is excised from the pig heart remnant to include a portion of the endocardium 22 containing the papillary heads 20 and the annulus as shown in FIG. 4. The papillary heads 20 are excised close to the endocardium 22 so that for each set of chordae tendineae 18 and papillary head 20, the entire chordae tendineae 18 and substantially the entire corresponding papillary head 20 is removed.

Figure 5:
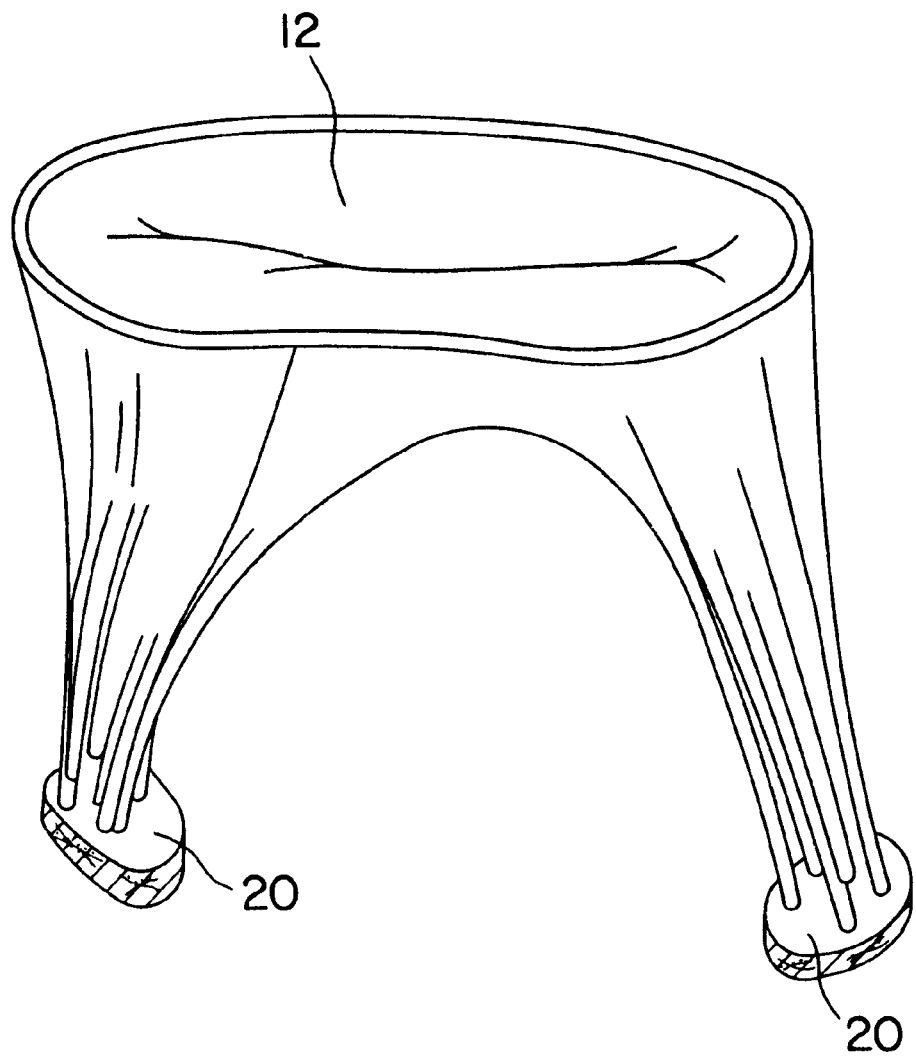
FIG. 5 is a perspective view of a fixed and trimmed porcine mitral valve ready to be completed to form a porcine mitral xenograft valve.

In the preferred embodiment of the invention, the excised mitral valve 12 is further fixed to complete fixation of the papillary heads 20. Then, the excess myocardial tissue is trimmed away and the mitral valve 12 is stored in fixing solution to await further processing as shown in FIG. 5.

The excess myocardial tissue trimmed away at this step is from two places. The first place where excessive myocardial tissue is trimmed from is around the annular tissue. Excess myocardial tissue here is tissue not supporting the annular tissue. Annular tissue is the tissue which supports the insertion of the leaflets into the valve's annulus.

The other place where excessive myocardial tissue is trimmed from is around the papillary heads. Excess myocardial tissue on the papillary heads is tissue that is not necessary to support the insertion of the chordae tendoneae into the papillary head tissue.

After the mitral valve 12 has been fixed, the valve 12 may be further processed. The processing could include adding a cloth covering to the mitral valve's annulus and adding a cloth covering to the mitral valve's papillary heads. An example of such processing is disclosed in my co-pending U.S. patent application Ser. No. 08/566,229 entitled "Physiologic Mitral Valve Bioprosthesis" filed Dec. 1, 1995. Then, the mitral valve 12 is preferably stored, according to techniques well understood in the art, for later use in constructing porcine mitral xenograft valves for human implantation.

Although the invention has been described in connection with xenograft heart valves, the invention may also be practiced on homograft or artificial heart valves. The modifications necessary to the disclosed invention to apply the invention to either a homograft or artificial heart valve will be clear to those skilled in the art.

The invention has been shown and described in connection with a specific embodiment. It is to be realized, however, that the description given herein is for the purpose of illustrating the invention and is not intended to be limiting. It is further understood that improvements and modifications to the disclosure made herein will occur to those skilled in the art and that such improvements and modifications will still fall within the scope of the invention.

What is claimed is:

1. A method for fixing a mitral valve in its natural geometry comprising the steps of:

(a) collecting a whole animal heart having myocardium, endocardium, a mitral valve having an annulus, chordae tendineae, papillary heads, left ventricle and left atrium shortly after the death of an animal;

(b) exposing, but not removing from the whole animal heart, the mitral valve, chordae tendineae and papillary heads of the animal heart such that major portions of the left ventricle and left atrium remain along with the exposed mitral valve, chordae tendineae, and papillary heads;

(c) fixing the entire result of step (b) to preserve the natural geometry of the mitral valve in situ with the major portions of the left ventricle and left atrium;

(d) excising tissue from the result of step (c), the excised tissue including the mitral valve, the annulus, and a portion of the endocardium containing the papillary heads, so that for each set of chordae tendineae and papillary head exposed in step (b), the entire chordae tendineae and substantially the entire corresponding papillary head are included in the excised tissue; and (e) retaining the excised tissue while disposing the remainder of the fixed result of step (c).

2. The method of claim 1 in which the animal is porcine.

3. The method of claim 1 in which the animal is ovine.

4. The method of claim 1 in which the animal is bovine.

5. The method of claim 1 in which step (c) comprises a technique chosen from the group consisting of zero pressure, low pressure, and high pressure fixation.

6. The method of claim 5 in which step (c) comprises applying at least one fixative agent chosen from the group consisting of glutaraldehyde, carbodyamides, and epoxides.

7. The method of claim 1 further comprising the step of:
completing fixation of the papillary heads.

8. The method of claim 1 further comprising the step of:
trimming away excess myocardial tissue from the fixed result of step (d).

9. A method for fixing a mitral valve from a heart comprising the steps of:
(a) collecting a whole animal heart having myocardium, endocardium, a mitral valve having an annulus, chordae tendineae, papillary heads, left ventricle and left atrium shortly after the death of an animal;
(b) exposing, but not removnig from the whole animal heart, the mitral valve, chordae tendineae and papillary heads of the animal heart such that major portions of the left ventricle and left atrium remain along with the exposed mitral valve, chordae tendineae, papillary heads;
(c) fixing the entire result of step (b) to preserve the natural geometry of the mitral valve in situ with the major portions of the left ventricle and left atrium;
(d) excising the tissue from the result of step (c), the excised tissue including the mitral valve, the annulus, and a portion of the endocardium containing the papillary heads, so that for each set of chordae tendineae and papillary head exposed in step (b, the entire chordae tendineae and substantially the entire corresponding papillary head are included in the excised tissue;
(e) retaining the excised tissue while disposing the remainder of the fixed result of step (c);
(f) completing fixation of the papillary heads; and,
(g) trimming away excess myocardial tissue from the fixed result of step (d).

10. A mitral valve fixed according to a method for fixing a mitral valve from a heart, the method comprising the steps of:
collecting a whole animal heart having myocardium, endocardium, a mitral valve, chordae tendineae, papillary heads, left ventricle and left atrium shortly after the death of an animal, the mitral valve having an annulus;
sectioning the left ventricle and left atrium of the animal heart thereby exposing the mitral valve, chordae tendineae and papillary heads of the animal heart, the resulting mitral valve, chordae tendineae, papillary heads and portions of the left ventricle and left atrium forming a heart remnant;
fixing the animal heart remnant including the mitral valve;
excising the mitral valve from the animal heart remnant to include the annulus, a portion of the endocardium containing the papillary heads so that for each set of chordae tendineae and papillary head, the entire chordae tendineae and substantially the entire corresponding papillary head is removed.

11. The valve of claim 10 wherein the animal heart is a porcine animal heart.

12. The valve of claim 10 wherein the animal heart is an ovine animal heart.

13. The valve of claim 10 wherein the animal heart is a bovine animal heart.

14. The valve of claim 10 wherein the step of fixing the animal heart remnant includes the step of fixing the animal heart remnant by a technique chosen from the group consisting of zero pressure, low pressure, or high pressure fixation.

15. The valve of claim 14 wherein the step of fixing the animal heart remnant by a technique chosen from the group consisting of zero pressure, low pressure, or high pressure fixation includes the step of applying fixative agents to the remnant, the fixative agents chosen from the group consisting of glutaraldehyde, carbodyamides, or epoxides.

16. The valve of claim 10 further comprising the step of:
fixing the animal heart remnant to complete fixation of the papillary heads.

17. The valve of claim 10 further comprising the step of:
trimming away excess myocardial tissue from the heart remnant.

18. The valve of claim 10 further comprising the step of:
trimming away excess myocardial tissue from the heart remnant.

19. A mitral valve fixed according to the method for fixing a mitral valve from a heart comprising the steps of:
collecting a whole animal heart having myocardium, endocardium, a mitral valve, chordae tendineae, papillary heads, left ventricle and left atrium shortly after the death of an animal, the mitral valve having an annulus;
sectioning the left ventricle and left atrium of the animal heart thereby exposing the mitral valve, chordae tendineae and papillary heads of the animal heart, the resulting mitral valve, chordae tendineae, papillary heads and portions of the left ventricle and left atrium forming a heart remnant;
fixing the animal heart remnant including the mitral valve;
excising the mitral valve from the animal heart remnant to include the annulus, a portion of the endocardium containing the papillary heads so that for each set of chordae tendineae and papillary head, the entire chordae tendineae and substantially the entire corresponding papillary head is removed;
fixing the animal heart remnant to complete fixation of the papillary heads;
trimming away excess myocardial tissue from the heart remnant.

* * * * *